United States Patent
Bittenson

(10) Patent No.: US 10,149,711 B2
(45) Date of Patent: Dec. 11, 2018

(54) SURGICAL IMPACT TOOL

(75) Inventor: Steven N. Bittenson, Raynham, MA (US)

(73) Assignee: DEPUY MITEK, LLC, Raynham, MA (US)

( * ) Notice: Subject to any disclaimer, the term of this patent is extended or adjusted under 35 U.S.C. 154(b) by 1678 days.

(21) Appl. No.: 13/435,644

(22) Filed: Mar. 30, 2012

(65) Prior Publication Data

US 2013/0261681 A1    Oct. 3, 2013

(51) Int. Cl.
*A61B 17/92* (2006.01)
*A61F 2/46* (2006.01)
*A61B 17/16* (2006.01)

(52) U.S. Cl.
CPC ............ *A61B 17/92* (2013.01); *A61F 2/4603* (2013.01); *A61B 17/1604* (2013.01); *A61F 2002/469* (2013.01); *A61F 2002/4681* (2013.01)

(58) Field of Classification Search
CPC ..... A61F 2/4603; B25D 11/064; B25B 19/00; B25B 21/02
USPC ..... 606/86 R, 99, 100, 86 A, 86 B; 173/117, 173/118, 121; 81/463, 464, 465, 466
See application file for complete search history.

(56) References Cited

U.S. PATENT DOCUMENTS

| | | |
|---|---|---|
| 974,267 A | 12/1909 | Hennessy |
| 1,753,454 A | 4/1930 | Weyandt |
| 3,054,464 A | 9/1962 | Ondeck |
| 3,712,390 A | 1/1973 | Berg |
| 3,938,018 A | 2/1976 | Dahl |
| 3,939,391 A | 2/1976 | Winnacker |
| 4,143,585 A | 3/1979 | Selsam |
| 4,237,987 A | 12/1980 | Sherman |
| 4,442,906 A | 4/1984 | Simpson |
| 4,468,594 A | 8/1984 | Jacquemet |
| 5,057,112 A | 10/1991 | Sherman |
| 5,079,459 A | 1/1992 | Huston |
| 5,108,400 A | 4/1992 | Appel |
| 5,167,043 A | 12/1992 | Lopez |
| 5,168,118 A | 12/1992 | Schroeder |
| 5,497,555 A | 3/1996 | Averbukh |
| 5,554,154 A | 9/1996 | Rosenberg |
| 5,603,740 A | 2/1997 | Roy |
| 5,666,715 A | 9/1997 | Zoiss |
| 5,903,134 A | 5/1999 | Takeuchi |
| 5,959,433 A | 9/1999 | Rohde |
| 5,980,528 A | 11/1999 | Salys |
| 6,112,830 A | 9/2000 | Ziegler |
| 6,184,651 B1 | 2/2001 | Fernandez |
| 6,288,519 B1 | 9/2001 | Peele |
| 6,342,776 B1 | 1/2002 | Taylor |
| 6,520,266 B2 | 2/2003 | Bongers Ambrosi |

(Continued)

FOREIGN PATENT DOCUMENTS

| | | |
|---|---|---|
| EP | 1584422 B1 | 10/2008 |
| EP | 2455006 A2 | 5/2012 |
| WO | WO 1995022934 A1 | 8/1995 |

*Primary Examiner* — Matthew Lawson
*Assistant Examiner* — Amy Sipp

(57) ABSTRACT

A surgical impact tool comprises an electromagnetic impactor hermetically sealed within a sterilizable housing having one or more external mechanical coupling for transmitting an impact to an object external to the tool. The housing also contains an energy storage medium rechargeable through the hermetic seal, and electronic controls operable through the hermetic seal.

17 Claims, 5 Drawing Sheets

(56) References Cited

U.S. PATENT DOCUMENTS

| | | | | |
|---|---|---|---|---|
| 6,520,269 | B2 | 2/2003 | Geiger | |
| 6,564,882 | B2 | 5/2003 | Durmeyer | |
| 6,603,284 | B2 | 8/2003 | Peele | |
| 6,644,418 | B2 | 11/2003 | Haga | |
| 6,648,568 | B2 | 11/2003 | Roseliep | |
| 6,884,264 | B2 * | 4/2005 | Spiegelberg | A61B 17/8802 606/92 |
| 6,918,449 | B2 | 7/2005 | Shinagawa | |
| 6,938,705 | B2 | 9/2005 | Kikuchi | |
| 6,960,214 | B2 | 11/2005 | Burkinshaw | |
| 6,991,459 | B2 | 1/2006 | Lashmore | |
| 7,001,393 | B2 | 2/2006 | Schwenke | |
| 7,121,360 | B2 | 10/2006 | Fünfer | |
| 7,303,556 | B2 | 12/2007 | Metzger | |
| 7,318,485 | B2 | 1/2008 | Greese | |
| 7,383,895 | B2 | 6/2008 | Aoki | |
| 7,407,070 | B2 | 8/2008 | Hezeltine | |
| 7,459,010 | B2 | 12/2008 | Johansson | |
| 7,504,802 | B2 | 3/2009 | Bersenev | |
| 7,569,057 | B2 | 8/2009 | Liu | |
| 7,622,892 | B2 | 11/2009 | Kim | |
| 7,667,431 | B2 | 2/2010 | Tilley | |
| 7,708,083 | B2 | 5/2010 | Dresig | |
| 7,708,739 | B2 | 5/2010 | Kilburn | |
| 7,784,562 | B2 | 8/2010 | Ikuta | |
| 7,789,282 | B2 | 9/2010 | Fukinuki | |
| 7,815,642 | B2 * | 10/2010 | Miller | 606/79 |
| 7,861,799 | B2 | 1/2011 | Iwakami | |
| 7,868,585 | B2 | 1/2011 | Sarnowsky | |
| 7,926,584 | B2 | 4/2011 | John | |
| 8,069,929 | B2 | 12/2011 | Sugimoto | |
| 8,147,511 | B2 * | 4/2012 | Perry et al. | 606/192 |
| 8,292,909 | B1 | 10/2012 | DuBois | |
| 8,393,409 | B2 | 3/2013 | Pedicini | |
| 8,602,124 | B2 | 12/2013 | Pedicini | |
| 8,695,726 | B2 | 4/2014 | Pedicini | |
| 8,870,872 | B2 | 10/2014 | Miller | |
| 2002/0079111 | A1 | 6/2002 | Camp | |
| 2003/0019645 | A1 * | 1/2003 | Artmann et al. | 173/117 |
| 2007/0282344 | A1 * | 12/2007 | Yedlicka | A61B 17/1615 606/80 |
| 2008/0115629 | A1 * | 5/2008 | Ayer et al. | 81/57.44 |
| 2008/0294142 | A1 * | 11/2008 | Patel | A61M 5/1413 604/506 |
| 2011/0257670 | A1 * | 10/2011 | Scortecci | 606/184 |
| 2011/0297407 | A1 * | 12/2011 | Sakai | 173/117 |
| 2012/0235501 | A1 * | 9/2012 | Kesler | H03H 7/40 307/104 |

* cited by examiner

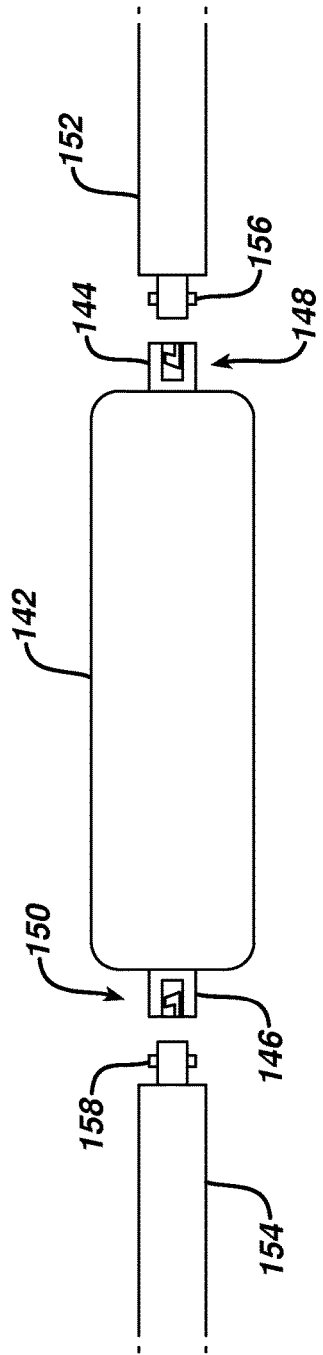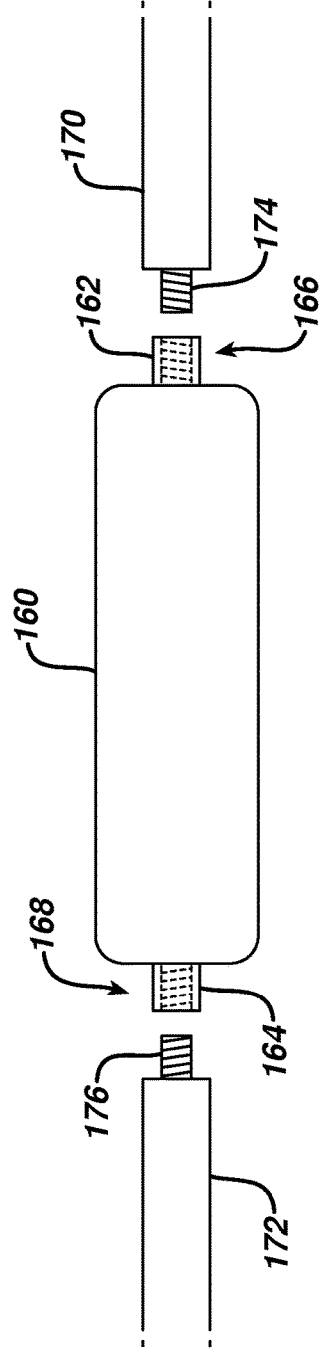

SURGICAL IMPACT TOOL

BACKGROUND

The present application relates to surgical tools and more particularly to rechargeable, electrically powered tools and methods for delivering impacts during surgical procedures.

Many orthopedic surgical procedures require a surgeon to deliver one or more impact to a surgical tool, an implantable prosthesis, a tissue fastener, or directly to a bone. For example, surgical hammers are used to position a knee implant or a hip implant with respect to a bone, or to drive a fastener such as a retaining pin, a bone nail or a tissue tack into bone, for repairing bone fractures or to reattach damaged tendons or ligaments to the bone. In addition, surgical impacts may be applied directly to bone to prepare a hole in the bone as part of a surgical procedure, or to create local defects such as microfractures in a bone surface to induce larger scale healing at the surgical site.

Current surgical impact tools are generally configured either as a conventional hammer having a weighted head mounted at an end of an elongated shaft, or as a weighted slug that is freely slidable along a shaft between two mechanical stops. An impact of the slug against one of the stops is transmitted to an end of the tool, which can include a fitting for temporary coupling to an implant, a fastener, or to another tool such as a bone fracture pick or awl. While providing more control in some surgical procedures than may be available using a conventional hammer, slide hammers can have disadvantages including relatively large dimensions along the direction of impact, and may require two-handed operation or additional assistance from a surgical associate.

As arthroscopic surgery becomes increasingly common, where orthopedic procedures are performed entirely via small portals opened through the patient's skin, precision in the positioning and gauging of surgical impacts becomes ever more critical to achieve desirable surgical outcomes. Both conventional hammers and slide hammers require the surgeon to perform relatively large-scale, abruptly terminated mechanical motions that can compromise this precision.

Electrically powered hammers are known in the construction arts and can include linear or rotary internal actuators for generating an impact, for example, as disclosed in U.S. patent application Ser. No. 09/741,786 to Camp, and U.S. Pat. No. 7,789,282 to Fukinuki et al., respectively, both of which are hereby incorporated by reference herein in their entirety, but such construction tools provide neither the control or sterility required for use in arthroscopic procedures, and a need exists for improved surgical impact tools.

SUMMARY OF THE INVENTION

A device for delivering a mechanical impact according to the present invention comprises a housing having an exterior surface and an interior surface, a wall forming a hermetic seal between the exterior and interior surfaces and defining an interior volume, and one or more coupling portion of the exterior surface configured for transmitting the impact from the housing to an object. The housing has a distal end, a proximal end and a tool axis between the ends.

Disposed within the interior volume is an electrically powered impactor for generating the impact at an impact-receiving portion of the interior surface, an electrical energy storage unit that can be recharged from outside the housing without violating the hermetic seal, and a controller configured for delivering electrical energy from the storage unit to the impactor for generating the impact. The controller is configured to receive a control signal through the wall without violating the hermetic seal.

The coupling portion of the housing can be configured to directly impact the external object, or to impact the object through an intermediate tool that can be releasably coupled to the housing. For example, the tool can be an implant insertion or extraction tool, or a microfracture pick.

In one aspect of the invention, the device has an elongated, generally cylindrical shape between the proximal and distal ends, and the impact is directed along the axis. The device can include a coupling at either or both of the distal and the proximal end for transmitting the impact to the object.

In another aspect of the invention, the storage unit is configured to be wirelessly charged through the wall, for example, via a magnetic field. In a further aspect of the invention, the controller is operated wirelessly using signals transmitted through the wall. The wall can be of any construction that can transmit charging and control signals to the components in the interior volume. In an, embodiment, the wall comprises a substantially continuous envelope about the interior volume and can be fabricated from metal. In an embodiment, the wall is nonmagnetic.

Preferably, the device can be operated single-handedly by a surgeon, where the surgeon can position and activate the device to deliver impacts without using a second hand or help from an assistant.

The device can be incorporated in a system for providing an impact at a surgical site in a patient. In addition to the device, the system includes one or more tool bit removably mountable to the device for delivering the impact from the tool to the surgical site, and a control transmitter positionable in proximity to the device for transmitting a signal to operate the device. The transmitter can be removably couplable to the device. Preferably, the device is sterilizable and in an embodiment, the control transmitter is provided in single-use sterile packaging Yet another aspect of the present invention is a method for delivering an impact at a surgical site. The method comprises identifying a location associated with the surgical site for delivering the impact; positioning a hermetically sealed, electrically powered impact tool at the location, and wirelessly activating the tool for delivering the impact.

A surgical hammer according to the present invention comprises a housing having an exterior surface and an interior surface with a wall providing a hermetic seal therebetween and defining an interior volume. The housing has a distal end and a proximal end. An electrically powered impactor is disposed within the interior volume and is configured for generating an impact at an impact-receiving portion of the interior surface. A surgical impact head couples to the housing exterior surface adjacent the impact-receiving portion of the interior surface whereby to receive the impact. An electrical energy storage unit is disposed within the interior volume and is rechargeable from outside the housing without violating the hermetic seal. A controller is disposed within the interior volume and is configured for delivering electrical energy from the storage unit to the impactor for generating the impact upon receipt of a control signal. The controller is configured to receive the control signal through the wall without violating the hermetic seal.

Preferably, the surgical impact head is releasably coupled to the housing exterior surface. The surgical impact head can be of various tool types such as an implant insertion tool, an implant extraction tool or a microfracture pick.

Preferably, the housing has a longitudinally extended, generally cylindrical shape between the proximal end and the distal end. In one aspect of the invention, a second surgical impact head is provided at an opposite end of the housing from surgical impact head.

In one aspect of the invention, the wall comprises a substantially continuous metallic envelope about the interior volume. In an aspect of the invention, the wall can comprise an optical window or an electrical feedthrough sealed therethrough.

Preferably, the storage unit is configured to be recharged wirelessly through the wall, and the controller is configured to receive the control signal wirelessly through the wall. The storage unit preferably comprises a storage capacitor.

In an aspect of the invention, the wall can be penetrated by a magnetic field or a radio frequency electromagnetic field for recharging the storage unit or receiving the control signal. A transmitter can be releasably coupled to the exterior surface of the housing and configured to transmit the control signal to the controller. The transmitter can be disposed in a sheath about a portion of the device or a handle extending outward from the device.

A method according to the present invention provides for delivering an impact at a desired location in surgical site in a patient. The method comprises the steps of: positioning at the location a surgical hammer comprising an electrically powered impactor in a hermetically sealed housing, and a surgical impact head coupled thereto; and activating the impactor to deliver an impact through housing to the surgical impact head at the location.

Preferably, the surgical hammer delivers a plurality of periodic impacts at the location.

In an aspect of the invention, the steps of positioning and activating the impactor are performed using a single hand.

Preferably, the step of activating the impactor is performed by wirelessly transmitting a control signal to the impactor through the housing, such as via a transmitter releasably coupled externally to the housing.

A system according to the present invention is adapted to provide an impact to a surgical site in a patient. The system comprises a hermetically sealed, rechargeable impact tool; and a control transmitter configured for transmitting a control signal to operate the tool to deliver one or more impact.

Preferably, one or more surgical tool bits are removably couplable to the impact tool.

Preferably, the control transmitter is releasably couplable to the impact tool.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 4A illustrates an embodiment of an impact tool according to the present invention configured with proximal and distal bayonet-type tool couplings;

FIG. 4B illustrates an embodiment of an impact tool according to the present invention configured with proximal and distal screw-threaded tool couplings;

DETAILED DESCRIPTION

Figure 1:
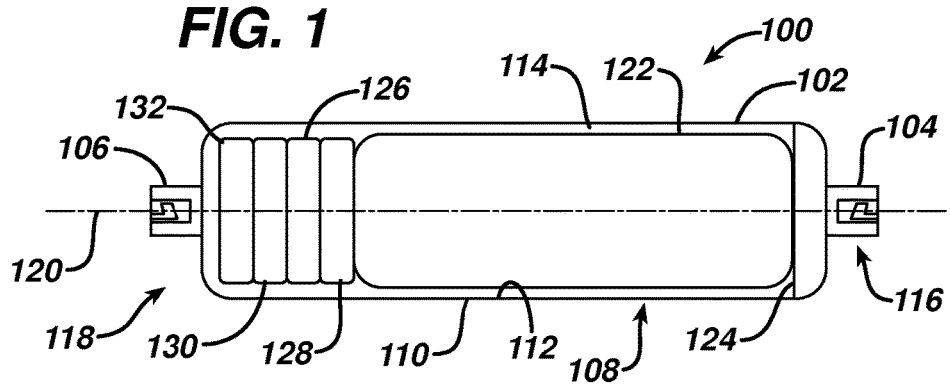
FIG. 1 is a functional block, cross sectional illustration of a surgical impact tool embodiment according to the present invention.

FIG. 1 is cross sectional schematic diagram illustrating functional aspects of an exemplary surgical impact tool 100 according to the present invention. The tool 100 comprises a housing 102 having one or more impact coupling portion 104, 106 for coupling to an external object such as a tool bit or a surgical implant (not illustrated in FIG. 1). The one or more coupling portion 104, 106 can be a mechanical fitting for releasably coupling to an external component, or a selected or modified surface portion of the housing 102, such as a flat portion, a protruding portion, or a depressed portion configured for sustaining multiple mechanical impacts with a selected external object. The one or more coupling portion 104, 106 can also comprise a tool end permanently mounted to or extending integrally from the housing 102.

The housing comprises a wall 108 having an exterior surface 110 and an interior surface 112, the wall 108 defining and hermetically enclosing an interior volume 114. The entire tool 100 is preferably sterilizable, the hermeticity of the wall 108 sealing all components within the interior volume 114 from the external environment of the tool 100, both during sterilization and during surgical use of the tool 100. The housing 102 and the location of the one or more coupling portion 104, 106 thereon can be of any configuration functional for delivering impacts to external objects. In the embodiment illustrated in FIG. 1, the housing 102 is generally cylindrical, and coupling portions 104, 106 are disposed at respective distal 116 and proximal 118 ends of the tool 100 along an impact axis 120. In other embodiments, the tool comprises a handle extending generally transversely from the axis 120. In still other embodiments, the one or more coupling portion 104, 106 is transversely displaced from the axis 120 on the housing 102.

An electrically-powered impactor 122 is disposed in the interior volume 114 and configured to deliver a mechanical impact to an interior impact-receiving portion 124 of the housing 102, for transmitting the impact via the wall 108 to the one or more coupling portion 104, 106 and thereby to the external object. In an embodiment, as illustrated in FIG. 1, the impactor 122 is configured to deliver an impact distally along the axis 120 and the impact-receiving portion 124 comprises a portion of the wall 108. In an embodiment, the impact-receiving portion 124 is a mechanically reinforced portion of the wall 108. In other embodiments, the impact-receiving portion 124 variously comprises a surface coating such as a resilient coating on the wall 108 to modify the impact, one or more mechanical members extending inwardly from respective lateral portions of the interior surface 112, or a structural member extending transversely through the axis 120 between lateral portions of the interior surface 112 of the wall 108.

The tool 100 further comprises a rechargeable (chargeable) electrical energy storage unit 126 disposed in the interior volume 114 and configured to store electrical energy for powering the impactor 122. The storage unit 126 can comprise any suitable electrical energy storage technology, with desirable properties including high discharge current for providing electrical pulses to the impactor, rapid charging capability, and high cycle life, that is, the ability to sustain many discharge-recharge cycles. In various embodiments the storage unit 126 comprises chargeable battery storage or capacitive storage. Either of these electrical energy storage technologies can be used for the storage unit 126. Present capacitor technology, using devices generally termed "ultracapacitors" desirably provides more rapid charging, higher discharge currents and greater cycle life than battery technology in an equivalently-sized package, whereas rechargeable battery technology may desirably provide greater total stored energy per charge than is available using an ultracapacitor.

In an embodiment, the tool 100 comprises a capacitor for electrical energy storage. A nonlimiting example of a capacitor suitably scaled for an embodiment of the inventive impact tool is the Model BCAP0350 ultracapacitor manufactured by Maxwell Technologies Inc., San Diego, Calif. This capacitor has a capacitance of 350 Farads at a rated voltage of 2.7 volts, and a rated life of 500,000 charge-discharge cycles. For illustrative reference only, an exemplary conventional, manually operated surgical hammer having a head mass of 0.5 kilogram may be used provide an impact force of approximately 1500 Newtons during a nominal four millisecond duration impact to a surgical tool or implant. This impact is roughly energetically equivalent to that generated by dropping the 0.5 kilogram mass from a height of seven meters to the impact target under the normal acceleration of Earth's gravity.

In an illustrative embodiment of an impactor according to the present invention comprising a 0.5 kilogram impact head, and with 50 percent utility of the electrical energy storable in a 350 Farad capacitor at 2.7 Volts, approximately twenty impacts substantially equivalent to the impacts according to the reference illustration above are deliverable from a single charge of the capacitor. In an embodiment, the 0.5 kilogram impact head comprises a magnetic material such as a magnetic steel alloy, and is approximately three centimeters in diameter and nine centimeters long. In a further embodiment, the impact head is electromagnetically accelerated using energy stored in the capacitor, over a longitudinal path 30 centimeters in length, to deliver the impact. Consistent with design constraints known to persons skilled in this art, the impact head mass, physical configuration, acceleration path length and energy storage parameters can be selected over a wide range of requirements for various surgical environments. For example, impacts optimized for driving a hip replacement stem into a femur may be much larger than those for driving a small diameter suture anchor into soft bone. In an embodiment, the impacts delivered by an impactor according to the present invention are adjustable down from a design maximum.

Also disposed in the interior volume 114 are functional elements corresponding to an electronic driver 128 configured to deliver energy from the storage unit 126 to the impactor 122, a charging receiver 130 for receiving electrical power from an external power source (not illustrated in FIG. 1) to charge the energy storage unit 126 without compromising the hermeticity of the wall 108, and communication electronics 132 configured to receive one or more type of communication signal from an external control interface (not illustrated in FIG. 1) for activating and controlling the impactor 122, also without compromising the hermeticity of the wall 108. In an embodiment, the communication electronics 132 further comprises one or both of bidirectional communication with, or providing electrical power to, the control interface. These functional elements can comprise known technologies including but not limited to power transistors for the electronic driver 128, inductive charging for the charging receiver 130, and magnetic, radio frequency, or optical coupling of communication signals for the communication electronics 132.

The functional elements illustrated in association with FIG. 1 can be arranged in any physical configuration and variously combined to provide a tool according to the present invention. By way of nonlimiting examples, the impactor 122 can comprise components useful for receiving externally applied energy to charge the energy storage unit 126, the driver 128 can be integrated with the communication electronics 132, all the electronic components can be integrated in a single physical unit, or electronic components can be distributed about or within the interior volume 114 or the impactor 122.

Figure 2A:
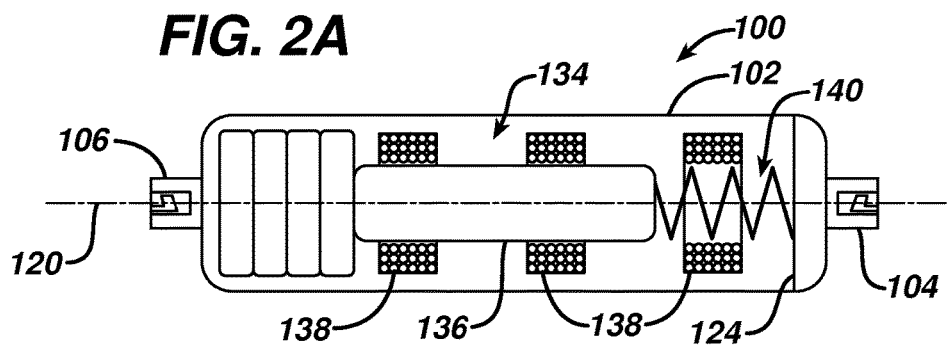
FIGS. 2A and 2B schematically illustrate exemplary embodiments of axially-biased impactors for a tool according to the present invention, in a schematic cross sectional views.
Figure 2B:
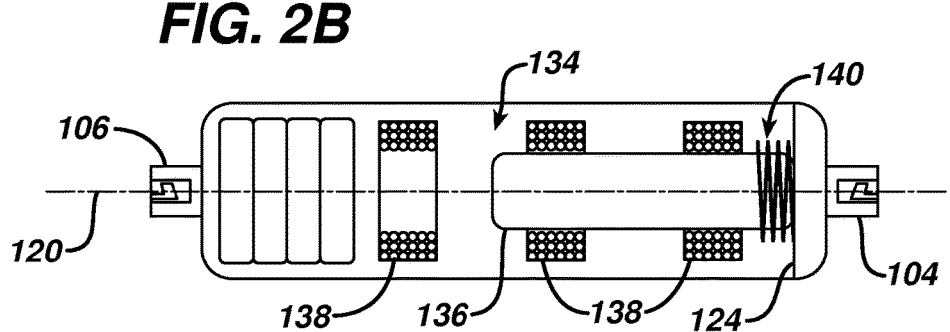

Impactors for tools according to the present invention can comprise any means for using electrical energy to generate an impact from within the tool, including rotary mechanisms such as a rotary solenoid or an electric motor incorporating a mechanical stop to a rotor component, and linear translation mechanisms such as electromagnetic solenoid-like structures, or piezoelectric translators. FIGS. 2A and 2B show in cross sectional views, illustrative embodiments of one type of impactor that can be used with the surgical impact tool 100 described hereinabove. FIGS. 2A and 2B illustrate a sliding-head impactor 134 comprising a weighted head 136 axially and slidably disposed with respect to one or more electromagnetic coil 138. In an embodiment, the head 136 is at least partially comprised of a ferromagnetic material. For illustrative purposes, electrical connections among the coils 138, as well as electrical connections among other components of the various embodiments of the tool 100, are not necessarily explicitly shown in the Figures herein, but are implied, the principles of such interconnections being understood by a person skilled in this art.

The head 136 is seen to be resiliently biased along the axis 120, for example, by a spring 140. In FIGS. 2A and 2B, the spring 140 is illustrated as anchored distally to the housing 102, but in other embodiments a spring or other biasing element can instead be anchored directly or indirectly at any longitudinal position with respect to the housing 102. In different embodiments, the head 136 is biased either proximally or distally along the axis 120.

In one embodiment, the spring 140 biases the head 136 proximally, illustrated as the head's axial position in FIG. 2A. In this embodiment, the spring 140 as illustrated in FIGS. 2A and 2B would be termed a compression spring. In this embodiment, upon electrically energizing one or more of the coils 138, in combination or in sequence, the head 136 is accelerated distally toward and impacts upon the impact-receiving portion 124 of the housing 102, at the head's axial position illustrated in FIG. 2B, whereupon the impact is transferred externally of the tool via the housing 102 and the one or more impact coupling 104, 106. In an embodiment, the quantity of energy delivered by the head 136 for the impact is determined electronically via a control signal. Following the impact, the one or more coil 138 is de-energized and the impact cycle is completed by the resilient bias relatively slowly returning the head 136 to the proximal axial position illustrated in FIG. 2A, the head 136 then being available for additional impact cycles.

In an alternate embodiment, the spring 140 biases the head 136 distally, illustrated as the axial head position in FIG. 2B. In this embodiment, the spring 140 would be termed an extension spring as illustrated in FIGS. 2A and 2B. In this embodiment, upon energizing one or more of the coils 138, in combination or in sequence, the head 136 is drawn proximally against the resilient bias toward but not necessarily entirely to the proximal position illustrated in FIG. 2A, storing energy in the spring as a function of the head's axial displacement from the distally biased position. At a predetermined proximal displacement of the head 136, or a preselected amount of energy delivered to the one or more coil 138, the one or more coil is de-energized, releasing the head 136 to accelerate under the resilient bias to impact the impact-receiving portion 124. Following the impact, the head 136 is available for additional impact cycles.

Figure 3:
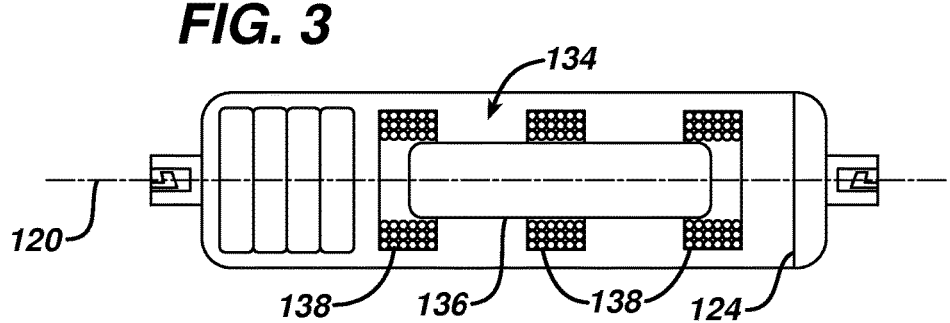
FIG. 3 schematically illustrates an axially non-biased embodiment of an impactor for a tool according to the present invention, in a schematic cross sectional view.

In yet another embodiment, illustrated schematically in FIG. 3, the impactor 134 includes minimal or no resilient biasing along the axis 120 and the head 136 is moved proximally and accelerated distally, primarily or entirely by energizing various ones of the one or more coil 138. In still another embodiment, the head 136 itself comprises one or more energizable electromagnet coil.

In the embodiments associated with FIGS. 2A, 2B and 3, the head 136 is accelerated distally to deliver an impact at the impact-receiving portion 124, but moved relatively slowly proximally, providing for stable handling of the tool 100. The one or more impact coupling portion 104, 106 can comprise one or more of a variety of coupling means to a tool bit or other external object. FIG. 4A schematically illustrates an impact tool 142 according to the present invention comprising exemplary twist-locking or bayonet-type coupling portions 144, 146 disposed respectively at a distal 148 and a proximal end 150 of the tool 142, for coupling to a tool bit or other device 152, 154 having respective complementary fittings 156, 158. FIG. 4B schematically illustrates another tool 160 according to the present invention comprising exemplary screw-threaded coupling portions 162, 164 disposed respectively at a distal 166 and a proximal end 168 of the tool 160, for coupling to a tool bit or other device 170, 172 having respective complementary fittings 174, 176. In other embodiments, only one of a distal and a proximal end of an impact tool according to the present invention comprises a coupling portion. In yet other embodiments, a coupling portion is disposed intermediate between distal and proximal ends of the tool. Additionally, any coupling means suitable for retaining a tool bit or otherwise coupling to an external object can be used as a coupling means within the scope of the present invention, for example, frictionally or interference fit tool couplings, or attachments including retaining latches, locks, or retaining members.

Referring again to FIG. 1, the wall 108 of the housing 102, in addition to providing hermeticity, sterilizability and impact resistance for operation of the tool 100, is configured to transmit energy from an external source to the interior volume 114 for charging the energy storage unit 126 via the charging receiver 128. The wall 108 is also configured to transmit communication signals to activate the impactor 122 via the communication electronics 132. The wall 108 can comprise a single, substantially continuous vessel about the interior volume, with charging energy and communication signals wirelessly transmissible through the material of the wall. Alternatively, the wall 108 can comprise a vessel constructed primarily of a first material and having one or more window of a second material hermetically sealed thereto, the window providing a port for transmitting one or both of charging energy and communication signals. Also alternatively, the wall 108 can comprise one or more hermetically sealed electrical feedthrough for transmitting one or both of charging energy and communication signals for the tool.

Figure 5A:
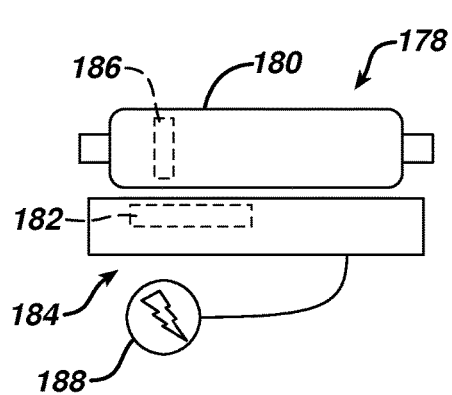
FIGS. 5A through 5C schematically illustrate exemplary electrical charging means for various embodiments of impact tools according to the present invention.
Figure 5B:
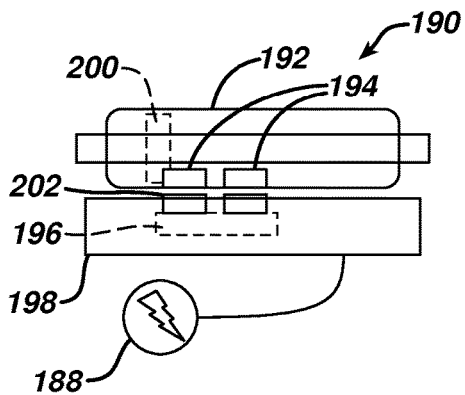
Figure 5C:
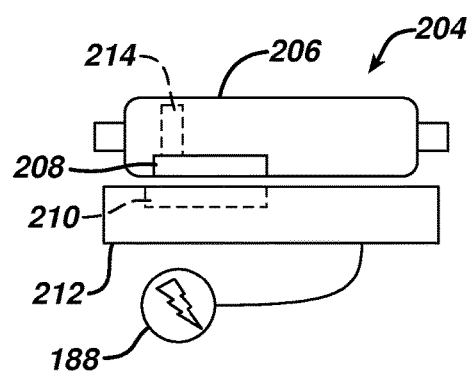

FIGS. 5A through 5C schematically illustrate exemplary embodiments of tools and associated charging means according to the present invention. First referring to FIG. 5A, a tool 178 comprises a substantially continuous hermetic wall 180 through which energy can be wirelessly transmitted from a charging transmitter 182 of a charging station 184 to a charging receiver 186 within the tool 178, for electrically charging an electrical energy storage device, not illustrated in FIGS. 5A-5C. In various nonlimiting embodiments, the charging receiver 186 is configured to be integral with other internal components of the tool 178, for example, communications electronics and driver electronics for an impactor that can be one of the impactor embodiments disclosed hereinabove or another impactor. In an embodiment, the charging station 184 is connected to a stationary electrical power source 188 such as an electrical utility outlet. The wall 180 can be sealed by welding, soldering, adhesives, compression, or any other means compatible with sterilization of the tool 178, and its use in a surgical instrument. Energy received via the receiver 186 is stored within the tool 178 for use in providing impacts when the tool 178 is used in a surgical procedure. In an embodiment, the wall 180 comprises a nonmagnetic metallic envelope that includes one or more of titanium, aluminum, a nonmagnetic stainless steel or another nonmagnetic metal. In another embodiment the wall 180 comprises an electrically nonconductive material that can include an impact-resistant ceramic or polymeric material, or an electrically nonconductive composite material.

A variety of means can be used to charge the tool 178, by which is meant storing electrical energy in an electrical energy storage unit within the tool 178. In one embodiment the transmitter 182 comprises a moving magnetic field or a moving magnet within the charging station 184 that induces a ferromagnetic component within the tool 178 to move in response, inducing a current in an electromagnetic coil to charge the tool 178. Referring to FIGS. 2A-3 as an example, in an embodiment, the tool 100 is charged by axially reciprocating the head 136 in response to an externally applied moving magnetic field, inducing a charging current in the one or more coil 138. Returning to FIG. 5A, in another embodiment the charging transmitter 182 comprises a source of vibration or an acoustic signal that transmits energy through the wall 180 to the receiver 186, which converts the vibrational or acoustic energy to electrical energy to charge the tool 178. In yet another embodiment, the transmitter 182 and the receiver 186 comprise an inductively-coupled charging system. In embodiments wherein the wall 189 is electrically nonconductive, charging can be performed using a radio-frequency wireless signal. In an embodiment, placement of the tool 178 on, in, or in proximity to the charging station 184 is sensed by the station 184, automatically initiating a charging cycle.

Now turning to FIG. 5B, a tool 190 according to the present invention comprises a hermetic wall 192 into which is hermetically sealed one or more electrical feedthrough 194 through which charging energy can be conductively routed from a charging transmitter 196 of a charging station 198 to a charging receiver 200 within the tool 190. In an embodiment, the charging station 198 is connected to the stationary electrical power source 188. The wall 192 and the one or more feedthrough 194 can be joined to one another and hermetically sealed together by welding, soldering, adhesives, compression, or any other means compatible with sterilization and use in a surgical instrument. Energy received via the receiver 200 via the one or more feedthrough 194 and corresponding electrical contacts 202 between the tool 190 and the charging station 198, is used to charge the tool 190. In addition to any of the wall materials discussed in association with the tool 178 of FIG. 5A above, the wall 192 of the tool 190 in the embodiment illustrated in FIG. 5B can comprise ferromagnetic materials. Many durable hermetic electrical feedthroughs are known in this art, including ceramic-to-metal seals well suited to harsh mechanical and chemical environments. The direct electrical connections used in this embodiment for charging the tool 190 allow high charging currents to be employed, for very rapid charging of the tool 190.

Now turning to FIG. 5C, an impact tool 204 comprises a hermetic wall 206 into which is hermetically sealed a window 208 through which charging energy can be wirelessly transmitted from a charging transmitter 210 of a charging station 212 to a charging receiver 214 within the tool 204. In an embodiment, the charging station 212 is connected to the stationary electrical power source 188. The wall 206 and the window 208 can be joined to one another and hermetically sealed together by any of the sealing means disclosed above, or by any other means compatible with sterilization and use in a surgical instrument. Energy received via the receiver is used to charge the tool 204. In one embodiment, the wall 206 is optically opaque and the window 206 is optically transparent for transmitting optical energy from the transmitter 210, comprising an optical emitter, to the receiver 214, comprising an optical receiver. In another embodiment, the window 208 is configured to transmit radiofrequency energy to which the wall 206 is otherwise opaque.

Figure 6A:
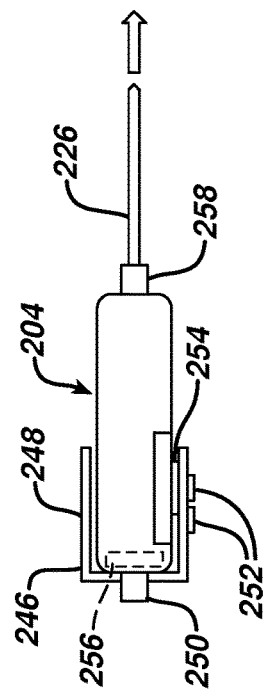
FIGS. 6A through 6E schematically illustrate exemplary control configurations for embodiments of impact tools according to the present invention.

The operation and control of impact tools according to the present invention can comprise any of a variety of interfaces. FIGS. 6A through 6E illustrate several exemplary embodiments of control interfaces for impact tools according to the present invention. Elements of these interfaces can be variously combined and modified, other interface elements can be employed, and their physical configurations can be adapted to meet specific ergonomic operating requirements, without deviating from the principles of the invention. First referring to FIG. 6A, illustrated with the tool 178 of FIG. 5A, a control interface 216 is shown to be configured for mechanical coupling to a proximal coupling portion 218 of the tool 178.

The control interface 216 is seen to comprise one or more control element 220 that in an embodiment includes one or more of an actuator switch and an impact adjustment control for setting the quantity of electrical energy imparted to the impactor to generate an impact. The control interface 216 also comprises a control transceiver 222 configured for wireless communication with communication electronics 224 within the tool 178. In one embodiment, the transceiver 222 comprises a radio frequency transmitter and the communication electronics comprises a radio frequency receiver. In a further embodiment, the transceiver also comprises a radio frequency receiver and the communication electronics also comprises a radio frequency transmitter. In another embodiment, the transceiver 222 and the communication electronics are configured to communicate using an acoustic signal. In yet another embodiment, communication between the transceiver 222 and the communications electronics 224 comprises positioning a magnet in the control interface 216 and detection of a magnetic field of the magnet using a magnetic sensor such as a Hall Effect Sensor in the communication electronics 224.

In one embodiment, the interface 216 comprises a battery for supplying electric power to operate the transceiver. In another embodiment, the interface 216 receives power wirelessly from the tool 178 for powering the transceiver 222. In yet another embodiment, one or both of the interface 216 and the tool 178 comprises a wireless identification device to facilitate communication between the devices. In a further embodiment the wireless identification device is a radio-frequency identification device (RFID). Also illustrated in FIG. 6A is an exemplary tool bit 226 coupled to a distal coupling portion 228 of the tool 178 for delivering a distally directed impact, illustrated by an arrow in the figure.

Figure 6B:
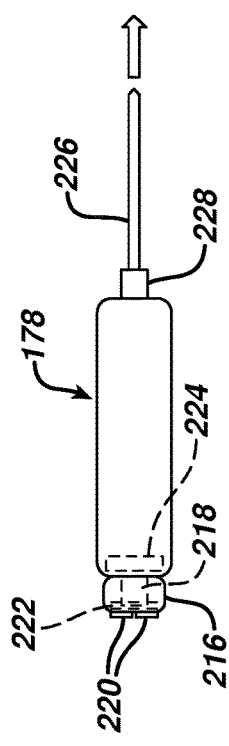

Now referring to FIG. 6B, illustrated with the tool 190 of FIG. 5B, a control interface 230 is shown to comprise a sheath 232 about at least a portion of the tool 190 and mechanically coupled to a proximal coupling portion 234 of the tool 190. In an embodiment, the sheath 232 comprises a soft or resilient material configured to absorb or dissipate a portion of an impact delivered by the tool 190. The control interface 230 is seen to include one or more control element 236 that can be an actuator switch or an impact adjustment control. The control interface 230 is also seen to comprise one or more electrical contact 238 for transmitting control signals to a control signal receiver 240 in the tool 190, via one or more hermetic electrical feedthrough 242. In an embodiment, electrical power for the control interface 230 is provided by the tool 190 via the one or more feedthrough 242. In another embodiment, the one or more hermetic feedthrough 242 is also used for charging the tool 190 when the tool is disposed in contact with a charging station. Also illustrated in FIG. 6B is the exemplary tool bit 226 coupled to a distal coupling portion 244 of the tool 190 for delivering a distally directed impact, illustrated by an arrow in the figure.

Figure 6C:
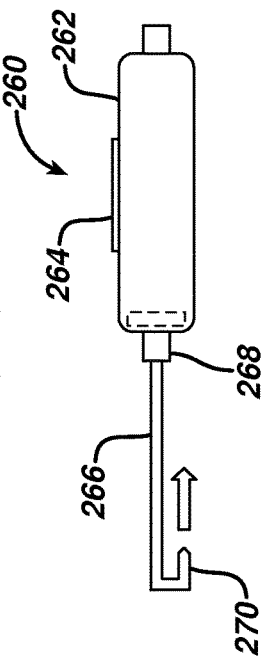

Next referring to FIG. 6C, illustrated with the windowed tool 204 of FIG. 5C, a control interface 246 is shown to comprise a sheath 248 about at least a portion of the tool 204. Whereas the interface 230 illustrated in FIG. 6B is shown as coupled to the proximal coupling portion 234 of the associated tool 190, the interface 246 illustrated in FIG. 6C does not couple to a proximal coupling portion 250 of the tool 204, leaving the proximal coupling portion 250 accessible for proximal coupling to a tool bit or other external object. The control interface 246 is seen to include one or more control element 252 that can be an actuator switch or an impact adjustment control, and a transceiver 254 configured to wirelessly communicate with communication electronics 256 in the tool 204. In one embodiment, the transceiver 254 and the communication electronics 256 comprise an optical communication system, comprising respective optical emitters and receivers. Also illustrated in FIG. 6C is the exemplary tool bit 226 coupled to a distal coupling portion 258 of the tool 204 for delivering a distally directed impact, illustrated by an arrow in the figure.

Figure 6D:
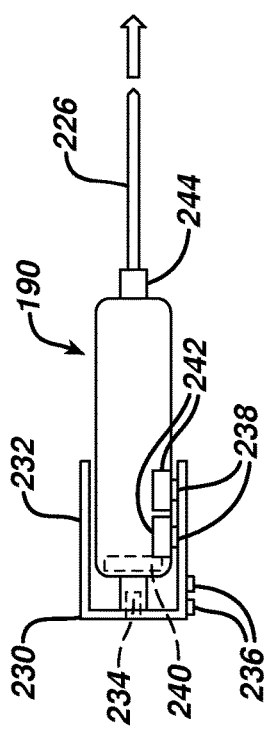

FIG. 6D illustrates a tool 260 according to the present invention comprising a hermetic wall 262 having an integral control interface 264. In one embodiment, the control interface 264 comprises one or more resilient member hermetically sealing an opening through the wall 262, wherein a mechanical force applied to flex the resilient member can engage an internal switch or other electrical device to provide a control signal to the tool 260. In an alternate embodiment, a tool according to the present invention is not hermetically sealed and control and activation of the tool comprises one or more non-hermetic penetration of a wall of the tool. Also illustrated in FIG. 6D is an exemplary proximal tool bit 266 coupled to a proximal coupling portion 268 of the tool 260 for delivering a distally directed impact via a hook-shaped tool tip 270, the direction of the impact illustrated by an arrow in the figure.

Figure 6E:
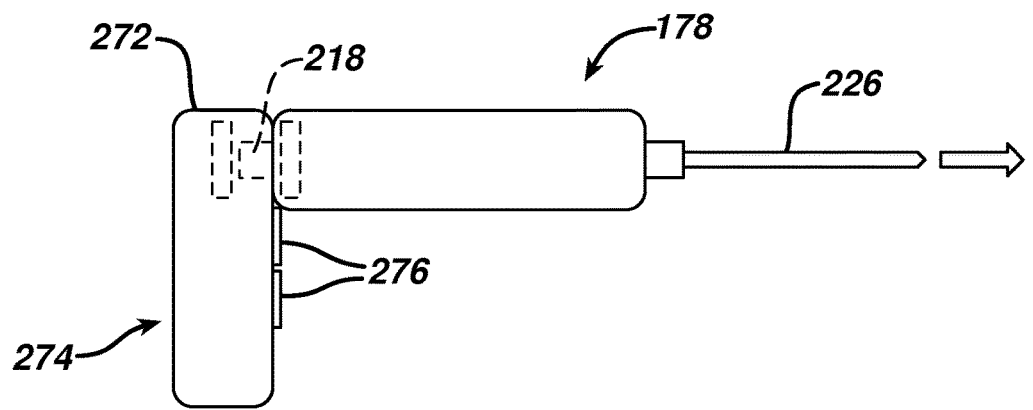

FIG. 6E illustrates a mechanical variation of the control interface 216 described in association with FIG. 6A, the interface 272 illustrated in FIG. 6E being configured to extend transversely from the tool 178. In an embodiment, the interface 272 comprises a pistol-type ergonomic handle 274 and one or more control element 276 positioned for convenient finger access when coupled to the tool 178. In various embodiments, any of the interfaces disclosed in association with FIGS. 6A through 6E comprises a single-use component selectable by a surgeon for use with an impact tool according to the present invention. In one embodiment, a selection of the interface is from among several available interfaces having different specifications from one another, the selection determining one or more of a repetition rate and a magnitude of an impact delivered by the impact tool. In an embodiment, the interface includes no internal power source, but is powered by the tool with which it is used. In another embodiment, the interface includes a readout that is configured to report the status of the charging of the tool.

Even further, in an embodiment comprising wireless communication between an impact tool according to the present invention and a complementary control interface, the tool can be operated remotely by the control interface, without the control interface being physically coupled to the tool, for example, by a surgical assistant, upon request of the surgeon. Alternatively, the control interface can comprise a wirelessly coupled footswitch for activation by the surgeon.

In an embodiment of a surgical procedure according to the present invention, a sterilized tool and one or more selected sterile-packaged interface according to the present invention are provided. In one embodiment, the tool is provided pre-charged to the surgeon. In another embodiment, the tool is charged using a charger located within or adjacent to the sterile surgical field, a step rendered practical for wirelessly charged tools by disposition of a sterile barrier between the tool and a potentially non-sterile charger. One of the one or more interface is removed from its sterile packaging and coupled to the tool to form a tool assembly. In an embodiment, a sterile surgical tool bit or an implant is also provided and coupled to the assembly.

To deliver an impact using the tool assembly, the surgeon grasps the tool and positions a working portion of the tool bit or implant at a desired location with respect to the patient. Then the surgeon then activates one or more control element associated with the interface to deliver one or more impact. In one embodiment, a single activation of the interface causes the tool to deliver a single impact. In another embodiment a single activation of the interface causes the tool to deliver a plurality of temporally spaced impacts. In an embodiment, the surgeon uses a single hand to perform at least two of grasping the tool, positioning the tool, and activating the interface to deliver one or more impact. In another embodiment, the surgeon uses a single hand to grasp the tool, position the tool, and activate the interface to deliver one or more impact. In one embodiment, the tool bit is a microfracture pick for performing a microfracture procedure on a bone. In another embodiment, the tool is directly coupled to an implant for impact driving the implant into bone without using an intermediate tool bit.

Advantageously, impact tools according to the present invention enable a surgeon to deliver controlled impacts using a single hand, freeing the surgeon's second hand to perform other surgical tasks, thereby providing opportunities to significantly enhance the surgeon's performance as well as potentially reducing the surgeon's dependence on surgical assistants during complex or delicate procedures such as arthroscopic procedures. Delivery of individual impacts or groups of impacts using impact tools according to the present invention can be controlled directly by a surgeon using controls incorporated into an interchangeable interface. Further, impact tools according to the present invention can be releasably coupled to any of a variety of surgical tool bits for use with or without applying impacts. In an embodiment, a cylindrically configured impact tool according to the present invention is coupled to a surgical screwdriver bit for rotating a screw-threaded surgical fastener, while providing the surgeon with an option to deliver impacts with the tool as needed.

Also advantageously, an impact tool according to the present invention can be repeatedly sterilized for multiple uses, and can be used in conjunction with simple, single use control interfaces selectable subject to surgeon preferences regarding control functions and ergonomics. In an embodiment, a single use interface according to the present invention is supplied to a surgeon in a sealed, sterile package. In another embodiment, an interface selectable by a surgeon is preprogrammed to provide impacts of one or more preselected intensity or temporal pattern.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A surgical hammer comprising:
   a housing having an exterior surface, an interior surface, and a wall forming a hermetic seal between the interior surface and the exterior surface and defining an interior volume, the housing having a distal end and a proximal end;
   an electrically powered impactor disposed within the interior volume and configured for generating an impact at an impact-receiving portion of the interior surface;
   a surgical impact head coupled to the housing exterior surface adjacent the impact-receiving portion of the interior surface whereby to receive the impact;
   an electrical energy storage unit disposed within the interior volume and rechargeable from outside the housing without violating the hermetic seal; and
   a controller disposed within the interior volume and configured for delivering electrical energy from the storage unit to the impactor for generating the impact upon receipt of a control signal, the controller configured to receive the control signal through the wall without violating the hermetic seal.

2. The surgical hammer according to claim 1 wherein the surgical impact head is releasably coupled to the housing exterior surface.

3. The surgical hammer according to claim 2 wherein the surgical impact head is one of an implant insertion tool, an implant extraction tool and a microfracture pick.

4. The surgical hammer according to claim 1 wherein the housing has a longitudinally extended, generally cylindrical shape between the proximal end and the distal end.

5. The surgical hammer according to claim 4 and further comprising a second surgical impact head at an opposite end of the housing from the surgical impact head.

6. The surgical hammer according to claim 1 wherein the wall comprises a substantially continuous metallic envelope about the interior volume.

7. The surgical hammer according to claim 1 wherein the wall comprises one of an optical window and an electrical feedthrough sealed therethrough.

8. The surgical hammer according to claim 1 wherein the storage unit is configured to be recharged wirelessly through the wall, and the controller is configured to receive the control signal wirelessly through the wall.

9. The surgical hammer according to claim 1 wherein the wall can be penetrated by at least one of a magnetic field and a radio frequency electromagnetic field for at least one of recharging the storage unit and receiving the control signal.

10. The surgical hammer according to claim 1 further comprising a transmitter releasably coupled to the exterior surface of the housing and configured to transmit the control signal to the controller.

11. The surgical hammer according to claim 10 wherein the transmitter is disposed in one or more of a sheath about a portion of the surgical hammer and a handle extending outwardly from the surgical hammer.

12. The surgical hammer according to claim 10 wherein the electrical energy storage unit comprises a capacitor.

13. A system for providing an impact to a surgical site in a patient, the system comprising
    a hermetically sealed, rechargeable impact tool; and
    a control transmitter configured for transmitting a control signal to operate the tool to deliver one or more impact.

14. The system according to claim 13 further comprising one or more surgical tool bit removably couplable to the impact tool.

15. The system according to claim 13 wherein the control transmitter is releasably couplable to the impact tool.

16. The system according to claim 15 wherein the impacting tool transmits electrical power to the control transmitter for transmitting the control signal.

17. The system according to claim 13 wherein the tool is sterilizable and the control transmitter comprises a single-use sterile package.

* * * * *